(12) United States Patent
Newkirk et al.

(10) Patent No.: US 7,629,014 B2
(45) Date of Patent: Dec. 8, 2009

(54) OILSEED PROCESSING

(75) Inventors: Rex W. Newkirk, Saskatoon (CA); David D. Maenz, Saskatoon (CA); Henry L. Classen, Saskatoon (CA)

(73) Assignee: MCN Bioproducts Inc., Saskatoon, Saskatchewan (CA)

( * ) Notice: Subject to any disclaimer, the term of this patent is extended or adjusted under 35 U.S.C. 154(b) by 490 days.

(21) Appl. No.: 11/362,860

(22) Filed: Feb. 28, 2006

(65) Prior Publication Data

US 2006/0147609 A1    Jul. 6, 2006

Related U.S. Application Data

(63) Continuation of application No. 10/255,599, filed on Sep. 27, 2002, now Pat. No. 7,090,887.

(30) Foreign Application Priority Data

Nov. 20, 2001   (CA)   ................................ 2363451

(51) Int. Cl.
    *A23L 1/20* (2006.01)
(52) U.S. Cl. .................. 426/634; 426/479; 426/489; 426/656
(58) Field of Classification Search .............. 426/634, 426/656, 479, 489
    See application file for complete search history.

(56) References Cited

U.S. PATENT DOCUMENTS

| 3,635,726 | A |   | 1/1972  | Sair |
|-----------|---|---|---------|------|
| 3,736,147 | A | * | 5/1973  | Iacobucci .................. 530/377 |
| 3,966,971 | A |   | 6/1976  | Morehouse et al. |
| 3,995,071 | A |   | 11/1976 | Goodnight, Jr. |
| 4,072,670 | A | * | 2/1978  | Goodnight et al. .......... 530/378 |
| 4,208,323 | A |   | 6/1980  | Murray et al. |

(Continued)

FOREIGN PATENT DOCUMENTS

CA    1100949    5/1981

(Continued)

OTHER PUBLICATIONS

Tzeng, Y.-M, Diosady, L.L. and Rubin, L.J. (1990) "Production of canola protein materials by alkaline extraction, precipitation, and membrane processing". *Journal of Food Science*, vol. 55, pp. 1147-1156.

(Continued)

*Primary Examiner*—Helen F Pratt
(74) *Attorney, Agent, or Firm*—Daphne L. Maravei; Blake, Cassels & Graydon LLP

(57) ABSTRACT

Crushed and de-fatted oilseed is extracted with water at neutral, mildly basic or mildly acidic pH; and is filtered. The filter media allows passage of small fragments of solid cell meat into the filtrate. The filtrate is treated with a base to increase pH to over pH 9, and solids are separated out. Protein is separated from other constituents of the liquid and concentrated, for example by heat-induced or isoelectric precipitation and/or ultrafiltration. The remaining liquid is rich in sugars. The process results in one or more protein products suited for human or animal food ingredients or for production of cosmetics, a sugar rich product suitable for fermentation or use as a feed ingredient, and a fiber-protein animal feed ingredient.

5 Claims, 4 Drawing Sheets

U.S. PATENT DOCUMENTS

| | | | | |
|---|---|---|---|---|
| 4,418,013 | A | | 11/1983 | Cameron et al. |
| 4,420,425 | A | * | 12/1983 | Lawhon ...................... 530/378 |
| 4,435,319 | A | | 3/1984 | Pearce |
| 4,677,065 | A | | 6/1987 | Buchbjerg et al. |
| 4,697,004 | A | * | 9/1987 | Puski et al. .................. 530/378 |
| 5,658,714 | A | | 8/1997 | Westfall et al. |
| 5,844,086 | A | | 12/1998 | Murray |
| 5,989,600 | A | | 11/1999 | Nielsen et al. |
| 7,226,633 | B2 | * | 6/2007 | Ishikawa et al. ............ 426/634 |

FOREIGN PATENT DOCUMENTS

| | | |
|---|---|---|
| EP | 925723 | 6/1999 |
| EP | 976331 | 2/2000 |
| GB | 1407773 | 9/1975 |
| GB | 2340727 | 1/2000 |
| WO | WO 9856260 | 12/1999 |
| WO | WO 0178521 | 10/2001 |
| WO | WO 0187083 | 11/2001 |

OTHER PUBLICATIONS

Blaicher, F.M., Elstner, F., Stein, W. and Mukherjee, K.D. (1983) "Rapeseed protein isolates: effect of processing on yield and composition of protein". *Journal of Agriculture and Food Chemistry*, vol. 31, pp. 358-362.

Friedman, M. (1996), "Nutritional value of proteins from different food sources". A review. *Journal of Agriculture and Food Chemistry*, vol. 44, pp. 6-29.

Prendergast, A.F., Higgs, D.A., Beames, R.M., Dosanjh, B.S. and Deacon, G. (1994) "Canola: Searching for subtitudes". *North. Aquacult.*, vol. 10, pp. 15-20.

Maenz, D.D. Engele-Schaan, C.M., Newkirk, R.W. and Classen, H.L. (1999) "The effect of minerals and mineral chelators on the formation of phytase-resistant and phytase-susceptible forms of phytic acid in solution and in a slurry of canola meal". *Ani. Feed. Sci. Tech.*, vol. 81, pp. 177-192.

Shaowen Wu et al. "Simplified process for soybean glycinin and beta—conglycinin fractionation". *Journal of Agriculture and Food Chemistry*, 48 (7) 2702-2708.

Taha F. S. et al. "Low-phytate protein concentrate and isolate from sesame seed". *Journal of Agriculture and Food Chemistry*, (1987), vol. 35, No. 3, pp. 289-292.

Newkirk, R.W., Classen, H.L., Scott, T.A. and Edney, M.J. "Commercial Desolventization Toasting Conditions Reduce The Content And The Availability Of Amino Acids In Canola Meal" (2000) *Poultry Sci.* vol. 79, suppl 1, p. 16, abstract 64.

* cited by examiner

OILSEED PROCESSING

This is a continuation of U.S. patent application Ser. No. 10/255,599, which was filed on Sep. 27, 2002 now U.S. Pat. No. 7,090,887.

This invention refers to the treatment of oilseed which has previously been crushed and has had oil extracted from it. Such oilseed will herein be called "defatted oilseed". Preferred oilseeds for the process of the invention are soybeans, canola (also called rapeseed), sunflower seeds, cottonseed, sesame seeds and safflower seeds. A particularly preferred defatted oilseed is canola flake, commonly known as white flake. Another preferred defatted oilseed is soybean meal.

Oilseeds typically contain from about 20 percent oil to about 40 percent oil, with the percentage varying with the type of oilseed. (All percentages given in this document are by weight). The seed is crushed and defatted in known manner, as by extraction with an organic solvent, followed by removal of the solvent. This known process removes all or most of the oil, and leaves a material known as an oilseed flake. Optionally, this flake can be toasted, and the product of such toasting is known as an oilseed meal. Both flake and meal are defatted oilseeds within the scope of this invention. Flake and meal are rich in protein. In some oilseeds, particularly canola, the protein has a good balance of essential amino acids, is of low molecular weight and is not highly allergenic to humans or animals. Some defatted oilseed also contains high levels of fibre, and the ease of removing this varies with the type of oilseed. However, such protein and fibre are not very useful commercially because of the presence of anti-nutritional factors in the defatted oilseed. Such factors include phytic acid or phytates (which are typically about 3 percent of canola flake and about 1.7 percent of soy meal) and also (in some oilseeds) poly-phenolic compounds. The presence of these anti-nutritional factors reduces the value of defatted oilseed as a nutritional supplement.

Accordingly, it is desirable to have a process which will treat a defatted oilseed to obtain a series of products of different composition, including a product which is rich in fibre, one or more products which are rich in protein, and a product which is rich in sugars.

GENERAL DESCRIPTION OF THE INVENTION

According to the invention, defatted oilseed is subjected to a series of sequential treatments. These will be called for the purpose of description Phases I-IV, although it will be understood that each phase need not follow immediately after the previous one, and that phases III and IV are performed on different intermediate products, and that other additional treatments can be interspersed or added if desired. Further, as discussed below, some phases are optional.

(a) Phase I Treatment

In phase I, a desolventized defatted oilseed is slurried in water at a pH of 3-9, with a preferred pH of from pH 7 to pH 9. The defatted oilseed is thoroughly mixed with the water. The temperature of mixing is not critical, but is preferred to be ambient temperature or above. It is particularly preferred to heat the mixture somewhat, to a temperature of 50° C.-95° C. as this increases solubility of some components of the defatted oilseed. Conveniently, heating can be done by preheating the water and then adding it to the defatted oilseed. The mixture is agitated to ensure thorough mixing. The period of agitation is not critical, and periods of for example 5 minutes to 2 hours are suitable. Following this, the slurry is filtered to separate most solid material from the liquid. Conveniently, this can be done by pressing, for example in a belt press, followed if desired by further filtration of the separated liquid ("depulping") to remove more solids. The filtration generates a liquid extract and a solid residue (known as "presscake"). Both the pressing and depulping can be carried out in multiple stages if desired to increase the liquid-solid separation.

Preferably, the machinery used for filtration permits the passage of small solid particles of the non-hull portion of the seed (known as "cell meats") to pass into the extract. These cell meats are high in protein. However, the machinery should not have openings large enough to allow passage of most of the seed hull parts and other fibre-enriched solids which are present in the de-fatted oilseed. The smallest openings are usually the filters in the depulping stage. Filters with openings of 25 microns are the smallest preferably used, and filters having openings of 2500 microns are the largest preferably used. Particularly preferred filters are filters having 50 micron openings to filters having 500 micron openings. Because defatted oilseed sometimes has cell meat particles which have a largest dimension of up to about 75 microns, the most preferred range of filters is from filters having 100 micron openings to filters having 250 micron openings. These most preferred filters will permit these cell meat particles to pass into the extract. Solids which are retained during the depulping stage are added to the solids retained during the pressing stage. These together are called "presscake" in this document.

The presscake typically has approximately 30-50% by weight of the dry matter in the original defatted oilseed, although this amount may vary depending on the type of oilseed used and the means used to separate it from the extract. It is dried in a conventional way, as for example by ring-drying or spray-drying to give a solid material which is suited to be a ruminant feed (called herein Phase 1 product). The Phase 1 product has an appreciable amount of protein (approximately 20-40% protein on a dry matter basis when the starting material is canola flake), and it also contains most of the poly-phenolic compounds and some of the phytic acid that was in the original defatted oilseed.

(b) Phase II Treatment

The extract from the Phase I treatment (which preferably contains small particles of cell meat) is treated with alkaline material (called herein Phase II treatment) to adjust its pH to a pH greater than pH 9. The preferred pH is 10.5 -11.5.

The treatment with alkaline material helps to solubilize some of the protein contained within the cell meat fragments in the extract recovered from phase I treatment. Further, the alkaline material selected can be one which will form insoluble phytate crystals which are easy to precipitate. For example, if the alkaline material is calcium oxide (CaO) or calcium hydroxide ($Ca(OH)_2$), then the phytic acid will react to form calcium phytate, which is insoluble and forms large crystals which precipitate easily from the filtrate at a pH over about pH 10, and can therefore be separated easily from the liquid phase of the extract, provided a pH of at least 10 is used. Similarly, other alkaline materials with divalent metal atoms tend to form large, easy to remove crystalline phytates at pH of over about 10, and such alkaline materials can be used if not otherwise objectionable (as for example because they are poisonous). Sodium hydroxide is less preferred as an alkaline material, because the phytate crystals it forms (sodium phytate) tend to be smaller and less dense than those of calcium phytate, and are thus less easy to separate.

Suitably, the treatment commences by adding CaO or $Ca(OH)_2$ until a pH of about 11 is reached. The pH adjustment is typically done with the extract at room temperature. Calcium phytate then precipitates out of the liquid. Optionally, the liquid is then heated to approximately 40-60° C. and agitated. The treatment with alkaline material (Phase II treatment) can last any suitable time necessary to precipitate out the majority of the phytates present. If it is desired to get out some of the phytates that are in the small solid particles of seed meat, a longer time may be needed than otherwise. Therefore, although the duration of the Phase II treatment is not critical, treatment times of 5 minutes—2 hours are found useful.

The preferred upper limit of the pH in Phase II treatment is pH 12. Good results can be obtained without using a higher pH than this, and a higher pH increases the likelihood of side reactions which could damage the protein in the treated liquid. However, a higher pH can be used where the risk of side reactions can be tolerated.

Solids in the extract after the pH adjustment (called herein Phase II solid) are removed from the remaining liquid. Any suitable process such as filtration or centrifugation can be used to separate the solids. The Phase II solid is highly enriched in phytate. If, as preferred, the alkaline material used for Phase II treatment was CaO or $Ca(OH)_2$, then the phytate will be calcium phytate. The Phase II solid is a novel material having at least 5% phytate, and preferably at least 10% phytate, together with a substantial amount of protein and some other matter, such as fibre. In the case of Phase II solid derived from canola flake, the Phase II solid typically has over 10% phytate and about 35-50% protein. The Phase II solid can be further reacted as set out below in Phase III to yield further products.

After removal of the Phase II solid, what remains is an alkaline liquid, called herein "Phase II liquid".

(c) Phase III Treatment (Optional)

Phase III is an optional process for the treatment of the Phase II solid.

The phase II solid can if desired be reacted with a suitable acid (for example HCl) to reduce the pH to about 1-5, preferably 2-4. This will be called herein "Phase III treatment", and is an optional part of the inventive process. The acid treatment serves to solubilize the phytate and phytic acid in the phase II solid. It yields a liquid phase which contains phytate (Phase III liquid) and a solid phase (Phase III solid). These can be separated in any convenient way, such as by centrifuging or filtering.

Optionally, the Phase III liquid can be treated with an enzyme preparation containing phytase either prior to or after separation of the Phase III liquid and Phase III solid. Phytase can hydrolyse all or part of the phytate in the Phase III liquid to yield inositol, a valuable food product.

After separation from the Phase III liquid, the Phase III solid is dried. The Phase III solid after drying contains below about 50% protein (the precise amount will depend on the defatted oilseed starting material) and also contains some fibre (the amount of which will also depend on the defatted oilseed starting material). For canola meal, the protein content is usually in the range 40-50%. The Phase III solid is product can suitably be used as an animal feed or as a human foodstuff. Optionally, it can be combined with a high protein source (as for example other products produced during phase IV, discussed below), to increase its feed or foodstuff value.

(d) Phase IV Treatment

Phase IV is an optional treatment for the Phase II liquid.

The liquid fraction from phase II treatment is rich in proteins, and can be treated for recovery of the proteins. Several optional processes can be used. One suitable process is ultrafiltration, to permit low molecular weight compounds to escape through the filter while retaining the protein. Another suitable process is to precipitate the proteins. The preferred methods of protein precipitation are heat induced curdling, by heating the liquid phase to a temperature of 70° C.-120° C. preferably 90° C.-110° C., for a short enough time so that the amino acid constituents of the proteins are not destroyed (for example about 5 minutes at 95° C.), or isoelectric precipitation through gradual addition of dilute acid until the pH of liquid approximates the isoelectric pH of the major proteins in the liquid, as known in the art for removal of proteins from solution. If proteins are precipitated, it is still preferred to use an ultrafiltration step following the precipitation, so as to remove any more soluble proteins that did not precipitate out.

The precipitated protein is then dewatered in known manner (as by filtration or centrifugation), and dried (as by ring driers or spray driers) to give a novel high value, high protein concentrate (phase IV product 1), which typically contains more than 80% protein, less than 1% phytate and which has a Protein Dispersibility Index of less than 5%. As used in this disclosure and the appended claims, Protein Dispersibility Index is calculated according to the AOCS (American Oil Chemists Society) Official Method Ba 10-65, as revised in 1999. The method provides a measure of water dispersible protein as a percentage of the total protein.

Phase IV product 1 is usable as animal feed or human food, or can be combined with other feeds or food to increase their protein content.

After the protein has precipitated out, the remaining liquid is preferably ultrafiltered, as for example by forcing it against a molecular sieve membrane. The retentate material which is retained by such filtration is a thick liquid, and it can be retained as a liquid or be dried by any conventional means to form a novel solid product (Phase IV Product 2). It is also protein rich. The protein concentration of Phase IV product 2 varies depending on the size of the molecular sieve filters used and the number of passes made through such filters, and can be from 50-100% protein, but will contain less than 1% phytate and have a Protein Dispersibility Index (as defined above) of greater than 40%. Phase IV product 2 is usable as animal feed or human food. It also is useful as an ingredient for skin lotions or cosmetics.

The remaining liquid (called herein Phase IV, product 3) is poor in protein and high in sugars. It is suited as a feed stock for ethanol fermentation, or it can be dried by any conventional means to recover the sugars. In a particularly preferred embodiment, Phase IV, product 3 is nanofiltered and the retentate is saved as Phase IV, product 4. The liquid which passes through the nanofiltration is mostly water, with some minerals. It can be discarded, or can be recycled to Phase 1, with the addition of make-up water, to be the water which is added to the defatted oilseed in Phase 1. The retentate (Phase IV product 4) has most of the sugars and residual protein that was in Phase IV product 3, but is more concentrated and with fewer impurities. Phase IV, product 4 can be dried or retained as a liquid. It is a good fermentation broth, and can be used as an animal feed ingredient or a human foodstuff.

DRAWINGS

The invention will be described further with respect to the drawings in which.

DETAILED DESCRIPTION

The invention will now be further described by reference to the drawings and with reference to examples showing the treatment of a typical defatted canola flake. This description relates to currently preferred embodiments of the invention, and modifications can be made without departing from the scope of the invention.

Figure 1:
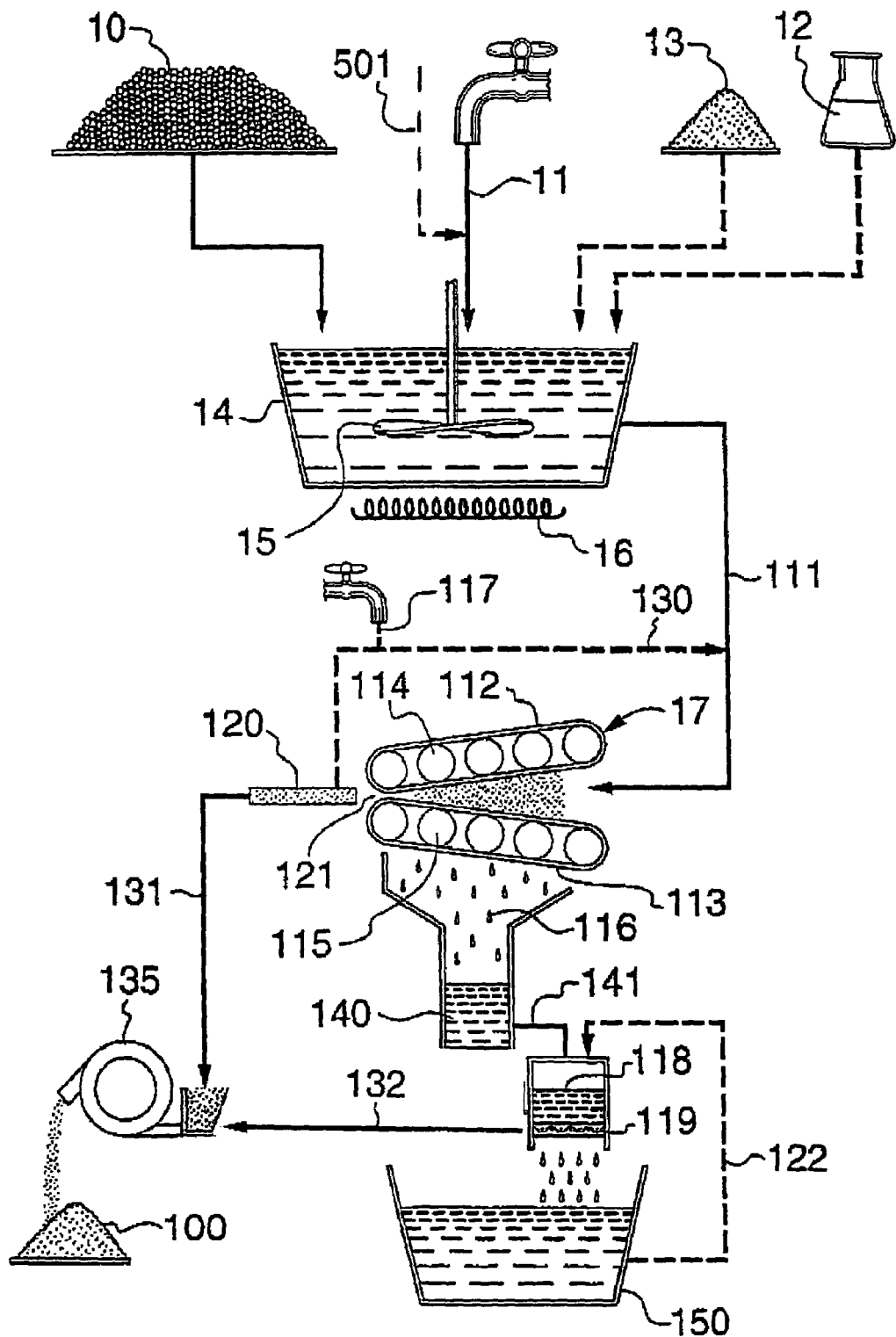
FIG. 1 is a flow chart of a process of treating defatted oilseed according to the invention. It corresponds to what is called Phase I treatment in the description.

Referring first to FIG. 1, desolventized defatted oilseed 10 is mixed with water 11 and optionally recycled water 501 from a later stage of the process (FIG. 4) in a reaction vessel 14 to make a slurry. Preferably the water is preheated before being added to the vessel 14. If necessary, the pH is adjusted by the addition of an acidic material (shown as acid 12) or an alkaline material (shown as calcium oxide 13) to a pH of 3-9. The slurry is agitated (shown schematically by the presence of agitator 15) and is optionally heated (shown schematically by the presence of heating coil 16).

After the water and oilseed are thoroughly mixed, the resulting slurry is then withdrawn by line 111 and is then pressed in belt press 17, which is shown schematically as having two belts 112 and 113 which run over rollers 114 and 115 respectively. The belts are oriented so that they gradually approach one another as the mixture passes through from right to left in FIG. 1. Extract is expressed from the mixture as shown schematically at 116 to collect at 140 in a suitable vessel. A moist solid presscake 120 is extruded from the nip 121 between the belts. The presscake 120 can be mixed with further water 117 and returned to the press for further pressing as shown at 130. When sufficient pressing has been done, the extract 140 is directed through line 141 to a mechanical depulper, shown schematically at 118. The depulper has a filter 119 on which solids (known as "pulp") deposits. The solids from the pressing and depulping are preferably sent (as shown by lines 131 and 132 respectively) for dewatering and drying as in ring drier 135 to yield a solid product 100 (Phase I product), which can be used as an animal feed for ruminants. The remaining extract 150 after depulping is collected. If desired, depulping be carried out several times, as shown by recycling line 122, before the extract 150 is collected.

Figure 2:
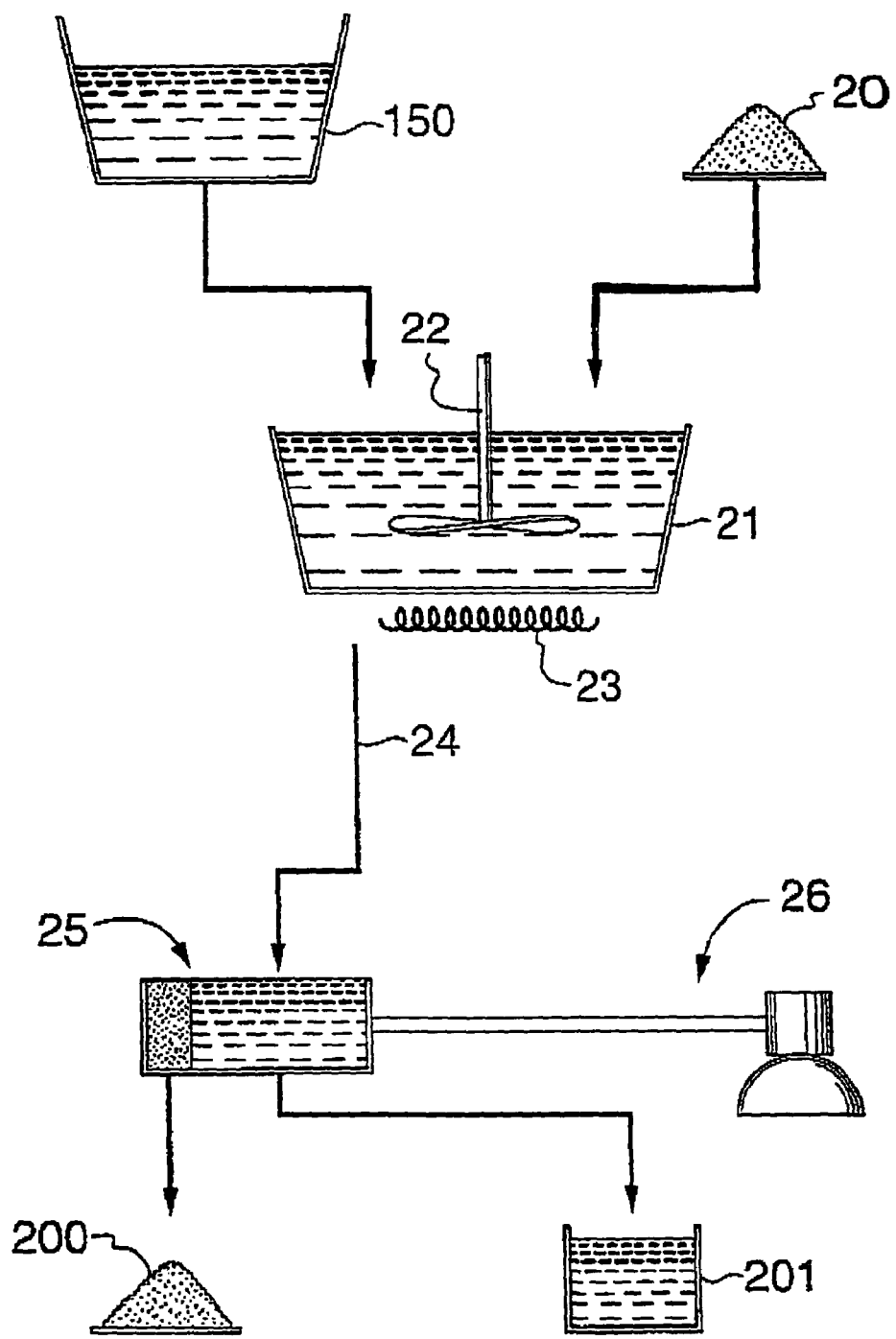
FIG. 2 is a flow chart of a process for treating the liquid obtained by the process of FIG. 1. It corresponds to what is called Phase II treatment in the description.

Referring now to FIG. 2, extract 150 is optionally mixed with alkaline material 20 (for example calcium oxide) to reach a pH of over pH 9 (preferably pH 10.5-11.5), and is heated in a reaction vessel 21 with agitation (as shown schematically at 22) and heating (as shown schematically by heating coil 23). Line 24 withdraws suitable amounts of the mixture to place in the bucket 25 of a bucket centrifuge generally indicated as 26. Solid and liquid components are separated out by centrifuging. A solid 200 (Phase II solid) is recovered. A liquid 201 (Phase II liquid) is also recovered.

Figure 3:
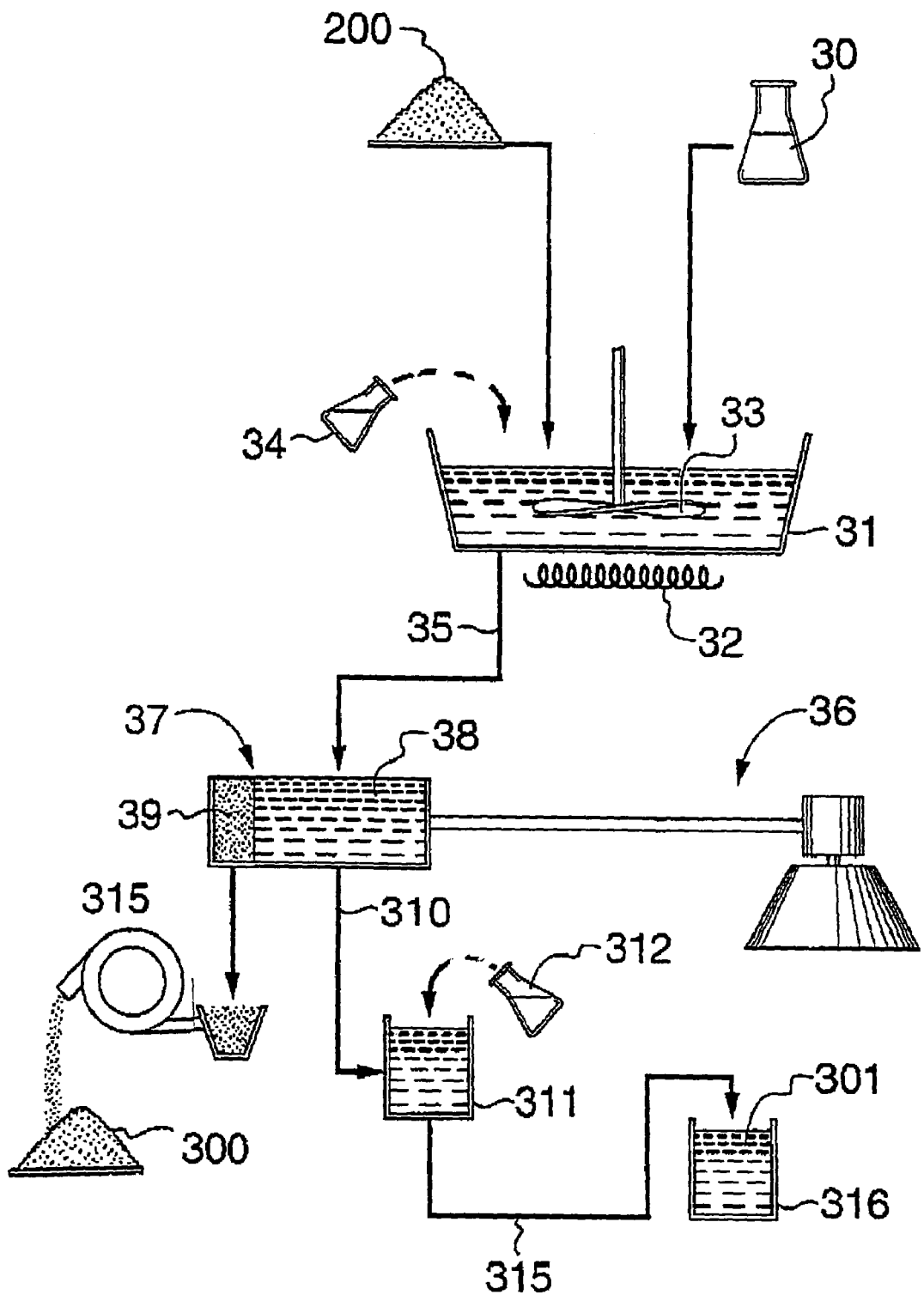
FIG. 3 is a flow chart of an optional additional process for treating the solid product of FIG. 2. It corresponds to what is called Phase III treatment in the description.

Referring now to FIG. 3, solid 200 is mixed with acid 30 and heated in a reaction vessel 31 as shown schematically by heating coils 32. The mixture is agitated, as shown schematically by agitator 33. Optionally, phytase 34 is added and agitation is continued. The mixture is then drawn off, as by line 35, to a centrifuge, generally shown as 36, where it is placed in the bucket 37 of the centrifuge. The mixture is then centrifuged until it separates into liquid 38 and solid 39. The solid 39 is removed and dried if necessary as by ring dryer 315 to form a solid product 300 which is useful as an animal feed or feed ingredient. The liquid 38 is drawn off as at 310 to a vessel 311. If phytase 34 has been added in vessel 31, this liquid 38 is rich in inositol. If phytase 34 has not been added, then the liquid is rich in phytate and can be treated with phytase by adding the phytase to vessel 311 as at 312. In either case, a product 301 which is a liquid rich in inositol is obtained. This is shown in the drawing as being drawn off by line 315 into container 316.

Figure 4:
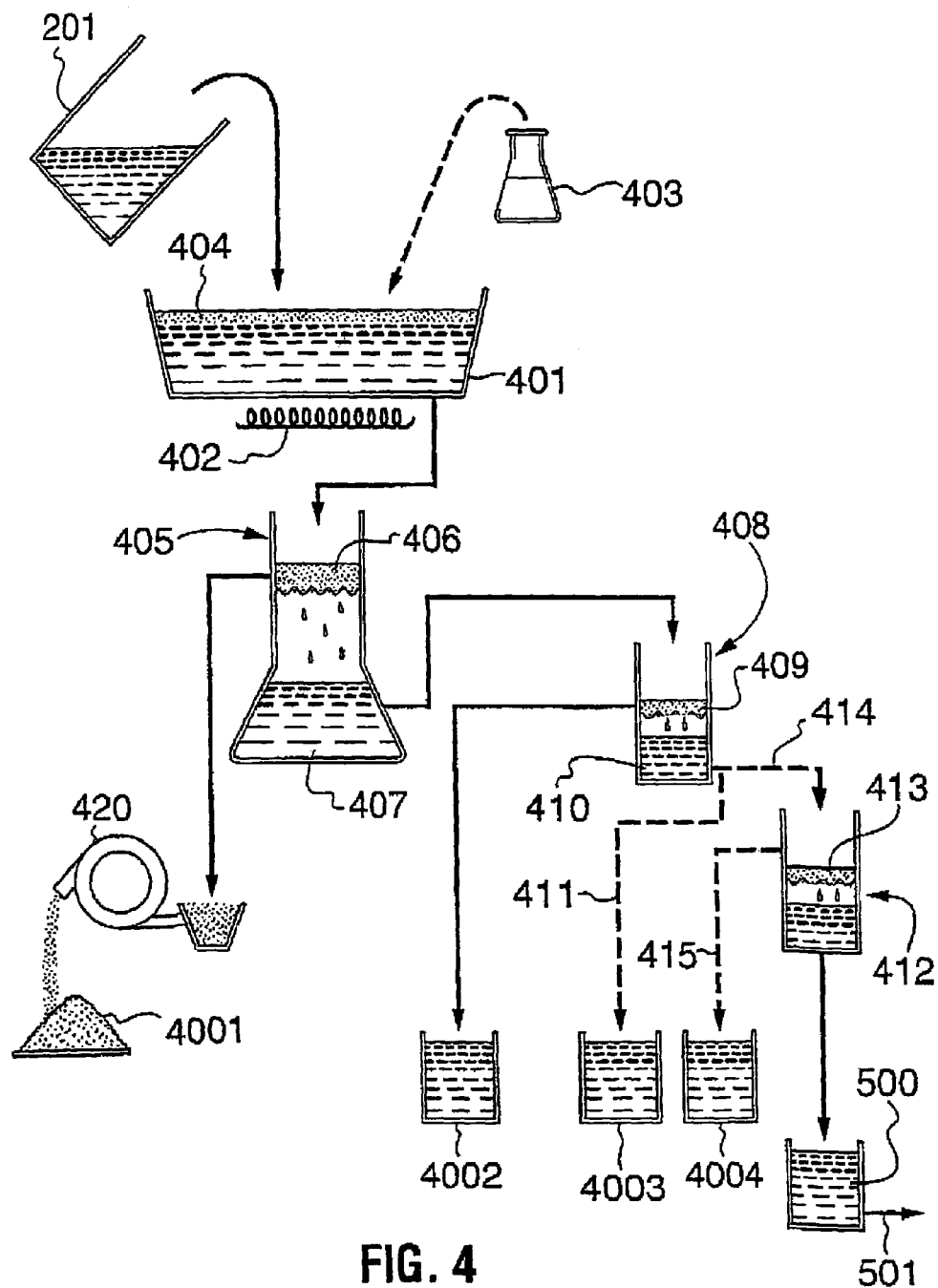
FIG. 4 is a flow chart of an optional additional process for treating the liquid product obtained by the process of FIG. 2. It corresponds to what is called Phase IV treatment in the description.

Referring now to FIG. 4, liquid 201 is treated to precipitate proteins as by heating it in a reaction vessel 401 (as shown schematically by the provision of heater 402) or by slow addition of acid 403, resulting in a curd 404 on the top of the liquid. The contents of the vessel 401 are then filtered or centrifuged to separate out the curd 404 as shown schematically by filter vessel 405, where the curd remains on the filter as a solid protein concentrate 406. The solid 406 is dried if desired as indicated schematically by ring dryer 420 to give product 4001 (Phase IV product 1). The liquid 407 which passes through the filter is subjected to ultrafiltration as shown schematically at 408 and the retentate 409 from such ultrafiltration is drawn off to become product 4002 (Phase IV, product 2). The retentate 409 is drawn off as a thick liquid, but may be dried to a solid if desired (not shown). Product 4002 is a high protein product which can be used as a human or animal food or as an ingredient for cosmetics and therapeutic products. The remaining liquid 410 after ultrafiltration is high in sugars. It can be recovered directly as shown by dashed line 411 to become product 4003 (Phase IV, product 3) which can optionally be used as a fermentation broth. Alternately, liquid 410 can be subjected to nanofiltration at 412, so that the sugars are concentrated as retentate 413, which is passed to a collection vessel to become product 4004 (Phase IV, product 4) as shown by dashed line 415.

The nanofiltration is not necessary, but serves to provide product 4004 which is in more concentrated form than product 4003, with less contamination from minerals. If the nanofiltration is carried out, the liquid 500 which passes through the filters comprises mostly water and minerals. It may be recycled to form part of the water input to vessel 14 in FIG. 1 or discarded, or its mineral content can be recovered.

The invention will now be illustrated by examples showing the treatment according to one preferred form of the invention of a defatted canola meal.

EXAMPLE 1

Initial Separation of Protein Rich Liquid and Ruminant Feed (Phase I Treatment)

25 kg of hexane-laden, oil-extracted canola white flake was obtained from a commercial oilseed crusher in Saskatchewan, Canada. Hexane was allowed to evaporate from the material at ambient temperatures until hexane could not be detected by a solvent detector to give a desolventized white flake. The desolventized white flake was roller milled to break up large clumps and produce a consistent starting material for extraction. It was then mixed with 75 kg of water that had been preheated to 50° C. and 1.7 L of a 10% slurry of CaO was added to the mixture. The material was mixed in a ribbon mixer until an even consistency was obtained. The pH of the mixture was tested and found to be 8.0. The material was then mixed for 10 minutes in the ribbon mixer.

The material was then passed through a continuous flow belt press (Frontier Technology Inc). The belt press compressed the material between two polypropylene monofilament belts which passed over a series of rollers which were gradually brought closer by a series of rollers as the material progressed through the press. The porosity of the belt was configured to allow an air passage rate of 0.17 cubic meters per second. The material was hand fed into the hopper of the press to provide an even flow of material between the belts. The material was separated into a liquid "extract" (herein called Phase 1 liquid) and a residual "presscake" (herein called Phase 1 solid) upon complete passage through the press. The Phase 1 liquid was then passed through a mechanical depulper with 150-micron openings. This depulping stage generated a further extract which passed through the screen and a residual pulp extract. The depulping procedure served to remove most fragments of hulls from the extract. The pulp was then added back to the presscake (Phase 1 solid) and the extracts from the depulping were added to the Phase 1 liquid.

In an optional step, the Phase 1 solid (presscake) was further treated. The presscake was mixed with 27 L of water at 50° C. in a ribbon mixer until an even consistency was obtained. This material was passed through the belt press as previously described to generate additional extract and presscake. The extract was depulped as previously described. The pulp was added to the presscake and the depulped liquid was added to the Phase 1 liquid.

The presscake from the second passage through the belt press was mixed with 23 L of water at 50° C. in a ribbon mixer until an even consistency was obtained. This material was passed through the belt press as previously described to generate additional extract and presscake. The extract was depulped as previously described and the pulp added to the final presscake (Phase 1 solid). The final presscake was analyzed for protein and dry matter, and the results are given in Table 1 below. The extract was added to the Phase 1 liquid.

Although repeated passages through the press are preferred and depulper yield a better separation, the invention contemplates a single pass if desired, and the result of the single pass would then be the Phase 1 product. In the table, the Phase 1 liquid and Phase 1 solid described are the products of three passes through each of the press and the depulper. These products were used in the subsequent examples.

EXAMPLE 2

Concentration of Phytates in Solid (Phase II Treatment)

The depulped extract from the three passes through the belt press (Phase 1 liquid) was placed in 100 L steam kettle and 1.7 L of a 10% slurry of CaO was added to the extract. During the extraction phase the temperature of the extract had dropped to ambient temperature. The pH of the extract at ambient temperature after addition of CaO was 11.0. The flow of steam to the kettle was turned on until the temperature of the extract was increased to 50° C. The extract was maintained at 50° C. with constant stirring in the kettle for a 30-minute period.

The extract was then centrifuged at 5000 times gravity for 2 minutes in a swinging bucket centrifuge. The supernatant was poured off and collected (Phase II liquid). The solid pellets from the centrifuge were resuspended in an equal volume of water (ambient temperature) and centrifuged again at 5000 times gravity for 2 minutes to wash residual soluble material associated with the pellets. The final pellets (Phase II solid) were combined and analyzed for protein, dry matter and phytic acid. The dry matter was found to contain 14.9% phytic acid and 45.17% protein.

EXAMPLE 3

Dephytinization of Solids (Phase III Treatment)

The Phase II solids generated in example 1 were stored and frozen until the day on which it was desired to do the Phase III treatment. However, if desired, Phase III treatment can be done immediately following phase II.

A 150 g fraction of stored and frozen Phase II solids was thawed. Four 10 g test batches were separated out from the fraction and each was mixed with 15 ml of water at room temperature. HCl was added to each test batch dropwise until the pH dropped to 3.5. The temperature of each test batch was then increased to 50° C.

Different amounts of phytase were added to each of the four test batches. The amounts were respectively 25, 15, 10 or 5 FTU (phytase units) of Natuphos® brand phytase (manufactured by BASF). One unit of phytase activity (1 FTU) is defined as the amount of the enzyme containing product that liberates 1 micromole of inorganic phosphorus per minute from an excess of sodium phytate at 37° C. and pH 5.5. The test batches were maintained at 50° C. with constant stirring after addition of the phytase. At times of 30 minutes, 60 minutes, 90 minutes and 120 minutes after the addition of the phytase, a 5 ml sample was removed from each test batch and was immediately mixed with 15 ml of ice cold 0.70 N HCl to denature the phytase.

Phytate was extracted from each sample by shaking for 3 hours at room temperature. The samples were then centrifuged at 16,000 times gravity for 10 minutes and the supernatant removed from each. 2.5 ml of chloroform was added to the supernatant and the material was centrifuged for 10 min at 10,000 times gravity, with the result that it formed two layers. The upper layer was removed and injected into the high pressure liquid chromatography unit. Phytate content was determined by the area of the phytate peak in comparison to the standard curve obtained with known quantities of phytate. Phytate content was also determined for a sample of the Phase II solids which had not been subjected to the treatment with phytase as described in this example. The untreated phase II solids had a phytate percentage of 14.90%, based on dry matter.

Table 1 shows the phytate content of the untreated solids and of the samples taken at each of the sampling time from addition of the phytase to the test batches. Dephytinization of the solids was dependent upon the amount of enzyme and duration of the reaction. With 25 FTU incorporated in the reaction mixture no phytate could be detected at 60 minutes from phytase addition. With 15 and 10 FTU in the mixture longer incubation periods were required to achieve complete dephytinization and with 5 FTU in the mixture residual phytate could still be detected 120 minutes after enzyme addition.

TABLE 1

Phytate content of solids (wt/wt % of dry matter) with no phytase addition (time 0) and after the various durations of incubation with the indicated levels of phytase.

| Time (min) | 25 FTU | 15 FTU | 10 FTU | 5 FTU |
|---|---|---|---|---|
| 0 | 14.90 | 14.90 | 14.90 | 14.90 |
| 30 | 1.48 | 3.14 | 4.98 | 6.94 |
| 60 | 0.00 | 0.74 | 1.07 | 2.85 |

TABLE 1-continued

Phytate content of solids (wt/wt % of dry matter) with no phytase addition (time 0) and after the various durations of incubation with the indicated levels of phytase.

| Time (min) | 25 FTU | 15 FTU | 10 FTU | 5 FTU |
|---|---|---|---|---|
| 90 | 0.00 | 0.00 | 0.00 | 2.85 |
| 120 | 0.00 | 0.00 | 0.00 | 1.42 |

EXAMPLE 4

Phase IV—Recovery of Protein-rich Materials

The supernatant obtained from centrifugation of the extract in Example 2 (Phase II liquid) was pooled and placed in 100 L steam kettle. The steam to the kettle was turned on such that the temperature of the extract reached 95° C. A temperature of 95° C. was maintained for 5 min and then cold water was then passed through the jacket of the steam kettle. Cold water was run for 20 minute period. A protein precipitant or curd formed on top of the extract during this heating and subsequent cooling procedure. The contents of the steam kettle were then poured through a 200 micron opening screen of nylon mesh sold under the trademark Nitex™ (Great Western Manufacturing Company, Inc.). The curd was collected in the screen while the liquid passed through the screen and was collected in a tub.

The curd was subsequently wrapped in the screen and placed in a 305 cm wide by 457 cm long by 152 cm high cheese mold. The mold was then placed in a cheese press and compacted by 10 minutes compression at 34 kPa, followed by 10 minutes compression at 69 kPa, followed by 10 minutes compression at 138 kPa, followed by 10 minutes compression at 207 kPa and a final 20 minutes of compression at 276 kPa The liquid expelled during compression of the mold was added to the liquid obtained from initial drainage through the screen. All of the liquid was combined together (Phase IV liquid). After the complete compression procedure, pressure was released and the protein curd (Phase IV product 1) was analyzed for protein, dry matter and phytate content.

The liquid remaining after separating the curd (Phase IV liquid) was passed through a 10,000 molecular weight cut off ultrafiltration membrane until the volume of the retentate decreased to approximately 20 L. 20 L of water was then added to the retentate and the filtration process was repeated (round 1 of diafiltration). A total of 6 rounds of ultrafiltration (also known as diafiltration) were run to concentrate the protein in the retentate. Liquid that had passed through the membrane (permeate) was collected and pooled. The final retentate was analyzed for protein, dry matter and phytate. (Phase IV product 2).

If desired, the permeate from the ultrafiltration could have been collected as a product (Phase IV product 3). However, this was not done in this example. Instead, the combined permeate from ultrafiltration was passed through a nanofiltration membrane until the volume of rententate had decreased to 18 L. The retentate (Phase IV product 4) was analyzed for protein, dry matter and phytate. The results are shown in table 2 below.

Table 2 also shows, under the heading "% recovery", the percentage of the protein which was in the original defatted oilseed which is recovered in the various products.

TABLE 2

Dry matter, protein and phytate contents of fractions obtained from processing of canola white flake. (phytate and protein content reported as % of dry matter.)

| Fraction | % Phytate | Dry matter | | Protein | | |
|---|---|---|---|---|---|---|
| | | Kg | % recovery | % | kg | % recovery |
| Defatted canola flake before process | 3.46 | 22.94 | — | 42.2 | 9.67 | — |
| Presscake (Phase I product) | — | 10.15 | 44.25 | 27.1 | 2.75 | 28.43 |
| Phase II solid product | 14.90 | 5.53 | 24.10 | 45.17 | 2.50 | 25.85 |
| Precipitant Protein (Phase IV product 1) | 0.70 | 2.67 | 11.64 | 94.87 | 2.54 | 26.27 |
| Ultrafiltrate Retentate (Phase IV product 2) | 0.00 | 0.93 | 4.05 | 75.02 | 0.69 | 7.14 |
| Nanofiltrate Retentate (Phase IV product 4) | 0.00 | 2.53 | 11.03 | 20.35 | 0.52 | 5.37 |

The Protein Dispersibility Index (as defined above) for Phase IV product 1 was 3.32 and for Phase IV product 2 was 52.46.

It will be understood that the forgoing description is by way of example only, and that variations of the forgoing process will evident to a person skilled in the art, while remaining within the invention.

What is claimed is:

1. A new composition of matter, being a product made from defatted canola flake and comprising at least 50% protein by weight of dry matter, less than 1% phytate by weight of dry matter and having a Protein Dispersibility Index of less than 5%.

2. A new composition of matter as claimed in claim 1 in which the product comprises at least 80% protein by weight of dry matter.

3. A new composition of matter, being a product made from defatted canola flake and comprising at least 50% protein by weight of dry matter, less than 1% phytate by weight of dry matter and having a Protein Dispersibility Index of greater than 40%.

4. A new composition of matter, being a product made from defatted canola flake and comprising from about 50% to about 75% protein by weight of dry matter, less than 1% phytate by weight of dry matter, and having a Protein Dispersibility Index of greater than 40%.

5. A new composition of matter as claimed in claim 4, having about 75% protein by weight of dry matter.

* * * * *